USOO5591439A

United States Patent [19]
Plotkin et al.

[11] Patent Number: 5,591,439
[45] Date of Patent: Jan. 7, 1997

[54] RECOMBINANT CYTOMEGALOVIRUS VACCINE

[75] Inventors: Stanley A. Plotkin, Paris, France; Robert P. Ricciardi, Glen Mills; Ewa Gonczol, Rosemont, both of Pa.

[73] Assignee: The Wistar Institute of Anatomy and Biology, Philadelphia, Pa.

[21] Appl. No.: 426,673

[22] Filed: Apr. 21, 1995

Related U.S. Application Data

[63] Continuation of Ser. No. 17,130, Feb. 12, 1993, abandoned, which is a continuation-in-part of Ser. No. 666,471, Mar. 6, 1991, abandoned, which is a continuation of Ser. No. 328,406, Mar. 24, 1989, abandoned.

[51] Int. Cl.$^6$ .................. A61K 39/12; A61K 39/235; A61K 39/245
[52] U.S. Cl. .................. 424/199.1; 424/230.1; 424/233.1; 435/5; 435/69.3; 435/172.3; 435/235.1; 536/23.1; 536/23.72
[58] Field of Search .................. 424/199.1, 230.1, 424/233.1; 435/5, 69.1, 69.3, 172.3, 235.1, 320.1; 536/23.1, 23.72; 436/543; 514/44

[56] References Cited

U.S. PATENT DOCUMENTS

| | | |
|---|---|---|
| 3,959,466 | 5/1976 | Plotkin . |
| 4,689,225 | 8/1987 | Pereira . |
| 4,920,209 | 4/1990 | Davis et al. .................. 435/235.1 |
| 5,124,440 | 6/1992 | Gehrz . |

FOREIGN PATENT DOCUMENTS

| | | |
|---|---|---|
| 0180288 | 5/1986 | European Pat. Off. . |
| 0236145 | 9/1987 | European Pat. Off. . |
| 0252531 | 1/1988 | European Pat. Off. . |
| 0252302 | 1/1988 | European Pat. Off. . |
| 0268014 | 5/1988 | European Pat. Off. . |
| 0271201 | 6/1988 | European Pat. Off. . |
| 0277773 | 8/1988 | European Pat. Off. . |
| 0389286 | 9/1990 | European Pat. Off. . |
| 0609580 | 8/1994 | European Pat. Off. . |
| WO89/07143 | 8/1989 | WIPO . |
| WO90/01497 | 2/1990 | WIPO . |
| WO90/06771 | 6/1990 | WIPO . |
| WO91/02004 | 2/1991 | WIPO . |
| WO91/18088 | 11/1991 | WIPO . |
| WO92/02628 | 2/1992 | WIPO . |
| Wo93/19191 | 9/1993 | WIPO . |
| WO94/17810 | 8/1994 | WIPO . |
| WO94/23744 | 10/1994 | WIPO . |

OTHER PUBLICATIONS

J. Hanshaw, "Congenital Cytomegalovirus Infection: A Fifteen Year Perspective", *J. Infec. Dis.*, 123(5):555–561 (May, 1971).
S. Plotkin et al, "Towne–Vaccine–Induced Prevention of Cytomegalovirus Disease after Renal Transplants", *Lancet*, 1:582–530 (Mar. 10, 1984) [Plotkin I].
S. Plotkin et al, "Clinical Trials of Immunization with the Towne 125 Strain of Human Cytomegalovirus", *J. Infect. Dis.*, 134(5):470–475 (Nov., 1976) [Plotkin II].
S. Plotkin et al, "Prevention of Cytomegalovirus Disease by Towne Strain Live Attenuated Vaccine", in *Birth Defects, Original Article Series*, 20(1):271–287 (1984) [Plotkin III].
J. Glazer et al, "Live Cytomegalovirus Vaccination of Renal Transplant Candidates", *Ann. Intern. Med.*, 91(5):676–683 (Nov., 1979).
Cranage et al., EMBO Journal, 5:3057–3063, 1986.
Alp et al., Journal of Virology, vol. 65, No. 9, 4812–4820, 1991.
M. Cranage et al, "identification of the Human Cytomegalovirus Glycoprotein B Gene and Induction of Neutralizing Antibodies via its Expression in Recombinant Vaccinia Virus", *EMBO J.*, 5(11):3057–3063 (Nov., 1986).
D. Johnson et al, "Abundant Expression of Herpes Simplex Virus Glycoprotein gB Using an Adenovirus Vector", *Virol.*, 164:1–14 (1988).
R. Dewar et al, "Synthesis and Processing of Human Immunodeficiency Virus Type 1 Envelope Proteins Encoded by a Recombinant Human Adenovirus", *J. Virol.*, 63(1):129–136 (Jan., 1989).
A. Davis et al, "Expression of Hepatitis B Surface Antigen with a Recombinant Adenovirus", *Proc. Natl. Acad. Sci. USA*, 82:7560–7564 (Nov., 1985).
J. Morin et al, "Recombinant Adenovirus Induced Antibody Response to Heptitis B Virus Surface Antigen in Hamsters", *Proc. Natl. Acad. Sci. USA*, 84:4626–4630 (Jul., 1987).
R. Couch et al, "Immunization with Types 4 and 7 Adenovirus by Selective Infection of the Intestinal Tract", *Am. Rev. Respir. Dis.*, 88;394–403 (1963).
E. Takafuji et al, "Simultaneous Administration of Live, Enteric–Coated Adenovirus Types 4, 7, and 21 Vaccines: Safety and Immunogenicity", *J. Infect. Dis.*, 140(1):48–53 (Jul., 1979).
P. Collis et al, "Adenovirus Vaccines in Military Recruit Populations: A Cost–Benefit Analysis", *J. Infect. Dis.*, 128(6):745–752 (Dec., 1973).
R. Stenberg et al, "Structural Analysis of the Major Immediate Early Gene of Human Cytomegalovirus", *J. Virol.*, 49(1):190–199 (Jan., 1984).
N. Alp et al, "Fine Specificity of Cellular Immune Responses in Humans to Human Cytomegalovirus Immediate–Early 1 Protein", *J. Virol.*, 65(9):4812–4820 (Sep., 1991).
GenBank data entry, Access #M11630, Code #HS5MIE4, (Sep. 15, 1989).
R. Lerner et al, "The Development of Synthetic Vaccines", in *The Biology of Immunologic Disease*, Chapter 31, pp. 331–338 (Spring, 1983).
H. Volkmer et al, "Cytolytic T Lymphocyte Recognition of the Murine Cytomegalovirus Nonstructural Immediate–Early Protein PP89 Expressed by Recombinant Vaccinia Virus", *J. Exp. Med.*, 166(3):668–677, Abstract (Sep., 1987).

*Primary Examiner*—Christine M. Nucker
*Assistant Examiner*—Laurie Scheiner
*Attorney, Agent, or Firm*—Howson and Howson

[57] ABSTRACT

The present invention provides a non-defective adenovirus recombinant expression system for the expression of the HCMV gB subunit and for the expression of non-structural immediate-early exon 4 proteins, said recombinant HCMV-expressing adenovirus being useful as a vaccine.

11 Claims, 3 Drawing Sheets

Ad-5/gB recombinant

RECOMBINANT CYTOMEGALOVIRUS VACCINE

This work was performed with government support under National Institutes of Health grants AI-07278 and HD-18957. The U.S. government has certain rights in this invention.

CROSS-REFERENCE TO RELATION APPLICATIONS

This is a continuation of U.S. patent application Ser. No. 08/017,130 filed Feb. 12, 1993, now abandoned, which is a continuation-in-part of U.S. patent application Ser. No. 07/666,471, filed Mar. 6, 1991, now abandoned which is a continuation of U.S. patent application Ser. No. 07/328,406, filed Mar. 24, 1989, now abandoned.

FIELD OF THE INVENTION

The present invention refers generally to a recombinant human cytomegalovirus vaccine, and more specifically to a subunit vaccine containing a HCMV major glycoprotein complex subunit gB gene.

BACKGROUND OF THE INVENTION

Cytomegalovirus (CMV) is one of a group of highly host specific herpes viruses that produce unique large cells bearing intranuclear inclusions. The envelope of the human cytomegalovirus (HCMV) is characterized by a major glycoprotein complex recently termed gB or gCI, which was previously referred to as gA. HCMV causes cytomegalic inclusion disease and has been associated with a syndrome resembling infectious mononucleosis in adults. It also induces complications in immunocompromised individuals.

CMV infection in utero is an important cause of central nervous system damage in newborns. Although the virus is widely distributed in the population, about 40% of women enter pregnancy without antibodies and thus are susceptible to infection. About 1% of these women undergo primary infection while pregnant. Classical cytomegalic inclusion disease is rare; however, a proportion of the infected infants, including those who were symptom free, are subsequently found to be mentally retarded.

Preliminary estimates based on surveys of approximately 4,000 newborns from several geographical areas indicate that the virus causes significant damage of the central nervous system leading to mental deficiency in at least 10% and perhaps as high as 25%, of infected infants. Assuming that about 1% of newborn infants per year excrete CMV and that about one fourth of those develop mental deficiency, in the United States this means approximately 10,000 brain-damaged children born per year. This is a formidable number, particularly in view of the ability of these children to survive [*J. Infect. Dis.*, 123 (5):555 (1971)].

HCMV in humans has also been observed to cause serious complications and infections in the course of organ transplantations, especially with kidney and liver transplants.

Several HCMV vaccines have been developed or are in the process of development. Vaccines based on live attenuated strains of HCMV have been described. [See, e.g., S. A. Plotkin et al, *Lancet*, 1:528–30 (1984); S. A. Plotkin et al, *J. Infect. Dis.*, 134:470–75 (1976); S. A. Plotkin et al, "Prevention of Cytomegalovirus Disease by Towne Strain Live Attenuated Vaccine", in Birth Defects, Original Article Series, 20(1):271–287 (1984); J. P. Glazer et al, *Ann. Intern. Med.*, 91:676–83 (1979); and U.S. Pat. No. 3,959,466.] A proposed HCMV vaccine using a recombinant vaccinia virus expressing HCMV glycoprotein B has also been described. [See, e.g., Cranage, M. P. et al, *EMBO J.*, 5:3057–3063 (1986).] However, vaccinia models for vaccine delivery are believed to cause local reactions. Additionally, vaccinia vaccines are considered possible causes of encephalitis.

Adenoviruses have been developed previously as efficient heterologous gene expression vectors. For example, an adenovirus vector has been employed to express herpes simplex virus glycoprotein gB [D. C. Johnson et al, *Virol.*, 164:1–14 (1988)]; human immunodeficiency virus type 1 envelope protein [R. L. Dewar et al, *J. Virol.*, 63:129–136 (1988)]; and hepatitis B surface antigen [A. R. Davis et al, *Proc. Natl. Acad. Sci., U.S.A.*, 82:7560–7564 (1985); J. E. Morin et al, *Proc. Natl. Acad. Sci., U.S.A.*, 84:4626–4630 (1987)]. Adenoviruses have also been found to be non-toxic as vaccine components in humans [See, e.g., E. T. Takajuji et al, *J. Infect. Dis.*, 140:48–53 (1970); P. B. Collis et al, *J. Inf. Dis.*, 128:74–750 (1973); and R. B. Couch et al, *Am. Rev. Respir. Dis.*, 88:394–403 (1963)].

There remains a need in the art for additional vaccines capable of preventing CMV infection by generating neutralizing antibody and cellular responses to CMV in the human immune system.

SUMMARY OF THE INVENTION

In one aspect, the present invention provides a non-defective recombinant adenovirus containing a gB or immediate-early exon-4 (IE-exon-4) subunit of the HCMV free from association with any additional human proteinaceous material. In this recombinant adenovirus, the HCMV subunit is under the control of regulatory sequences capable of expressing the HCMV gB or IE-exon 4 subunit in vitro and in vivo.

Another aspect of the present invention is a vaccine composition comprising a non-defective recombinant adenovirus, as described above.

In a further aspect, the invention provides a method of vaccinating a human against HCMV comprising administering to the patient the recombinant adenovirus containing the subunit gene encoding either gB or IE-exon-4, in a vaccine composition. The inventors have found that this method of presenting these HCMV genes to a vaccinate is particularly capable of eliciting a protective immune response.

In yet a further aspect the invention provides an adenovirus-produced HCMV IE-exon-4 subunit, which subunit may also form vaccine compositions to protect humans against HCMV.

In still a further aspect, the present invention provides a novel murine model useful for demonstrating cytotoxic T lymphocyte (CTL) response to individual HCMV proteins.

Other aspects and advantages of the present invention are described further in the following detailed description of preferred embodiments of the present invention.

Figure 1A:
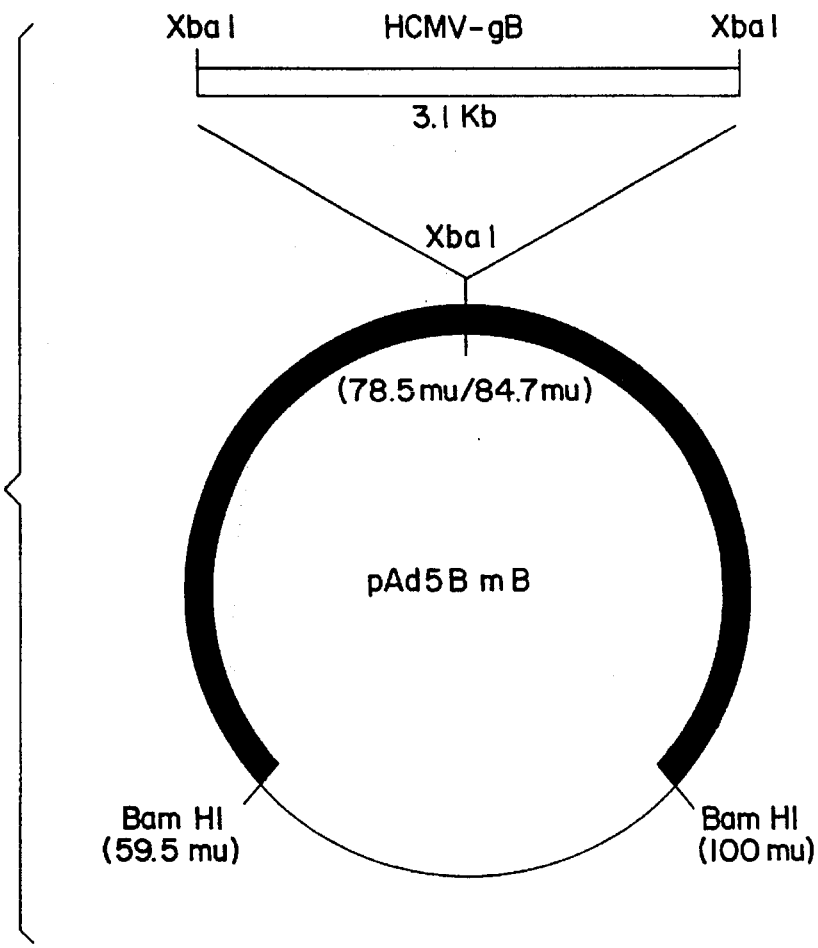
FIG. 1A illustrates diagrammatically the cloning of the gB gene into the early region 3 (E3) transcription unit of Ad5. Represented are the 3.1 kb fragment containing the gB gene by the open box; the adenovirus sequences extending from 59.5 to 100 mu (except for the deletion of the 78.5 to 84.7 mu length) by the filled portion of the circle: the large BamHI fragment of the pBR322 by the thin line of the circle. In the figures, the restriction enzymes are identified as follows: X is XbaI, B is BamHI.
Figure 1B:
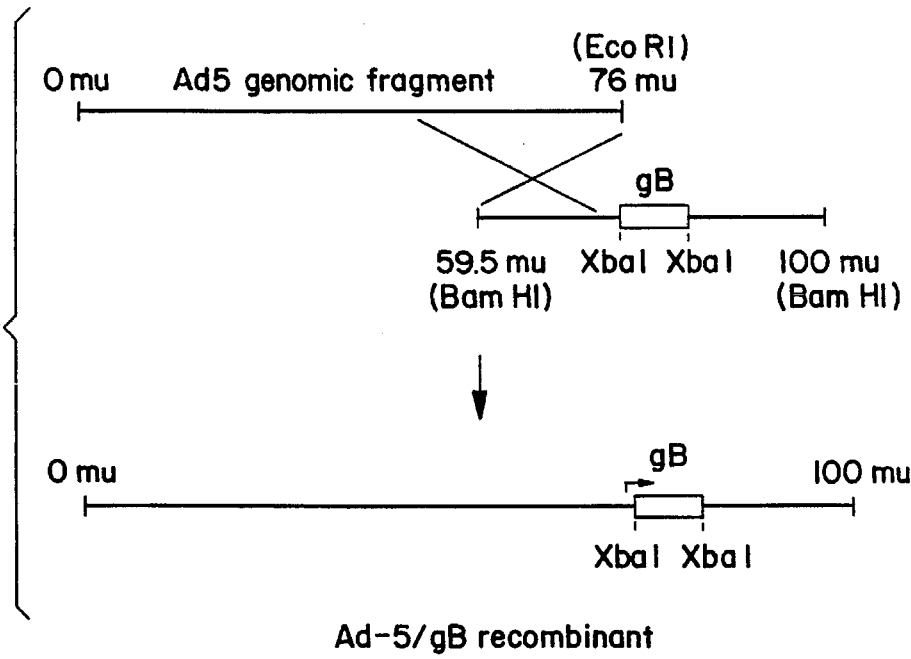

FIG. 1B illustrates diagrammatically the construction of the recombinant adenovirus virus Ad5/gB, containing the gB gene of the Towne strain of HCMV described in Example 1. This figure shows the 59.5 mu to 76 mu region where homologous recombination occurs (as indicated by the crossed lines) between wild type Ad5 viral sequence and the adenovirus sequences present on the pad5 plasmid containing the gB gene. The plaque purified recombinant virus retains the cloning XbaI sites and the direction of transcription of the gB gene from the E3 promoter is indicated by the bent arrow. Restriction enzymes are as identified above.

Figure 2A:
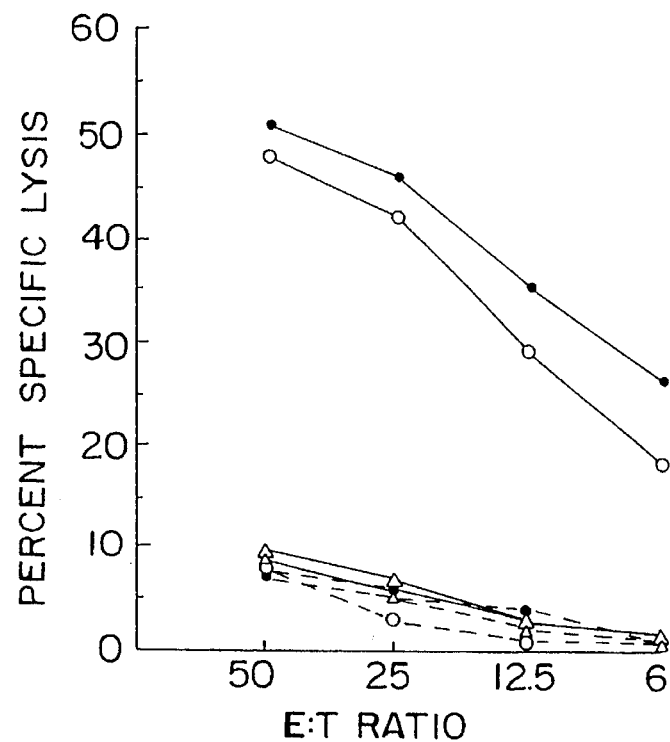

FIG. 2A illustrates HCMV-gB-specific CTL responses in CBA mice immunized i.p. with the recombinant, known as Ad-5/gB or Ad-gB, as described in Example 6. The closed squares indicate uninfected cells; closed circles indicate Ad-5 E3-infected cells; open circles indicate VacC-gB-infected cells; and delta (triangle) indicates WT-Vac infected cells. In the graph, a solid line connecting the above symbols indicates that the target cells were L-929 cells. A dotted line connecting the symbols indicates that the target cells were MC57 cells.

Figure 2B:
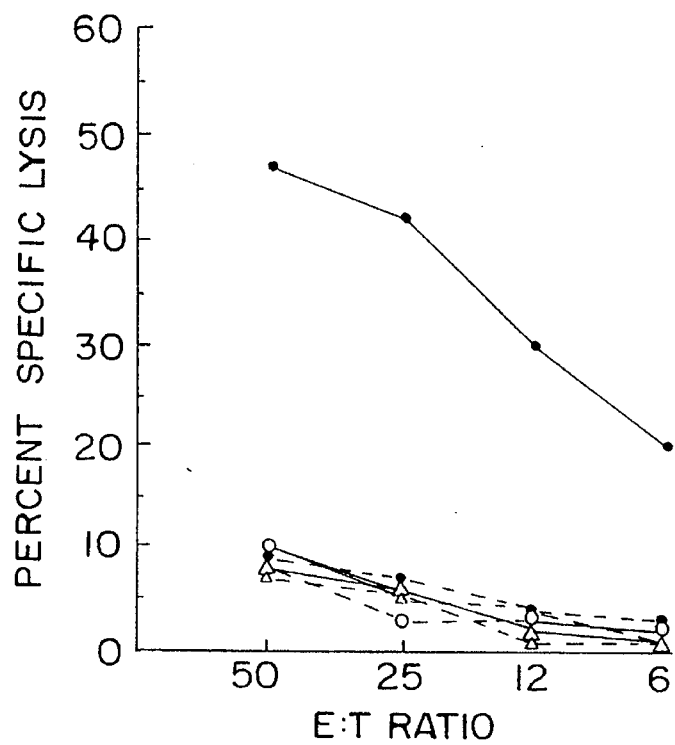

FIG. 2B illustrates the ability of in vitro restimulated spleen cells from CBA mice immunized with WT-Ad to lyse various target cells as described in Example 6. The symbols and lines are as described for FIG. 2A.

Figure 3:
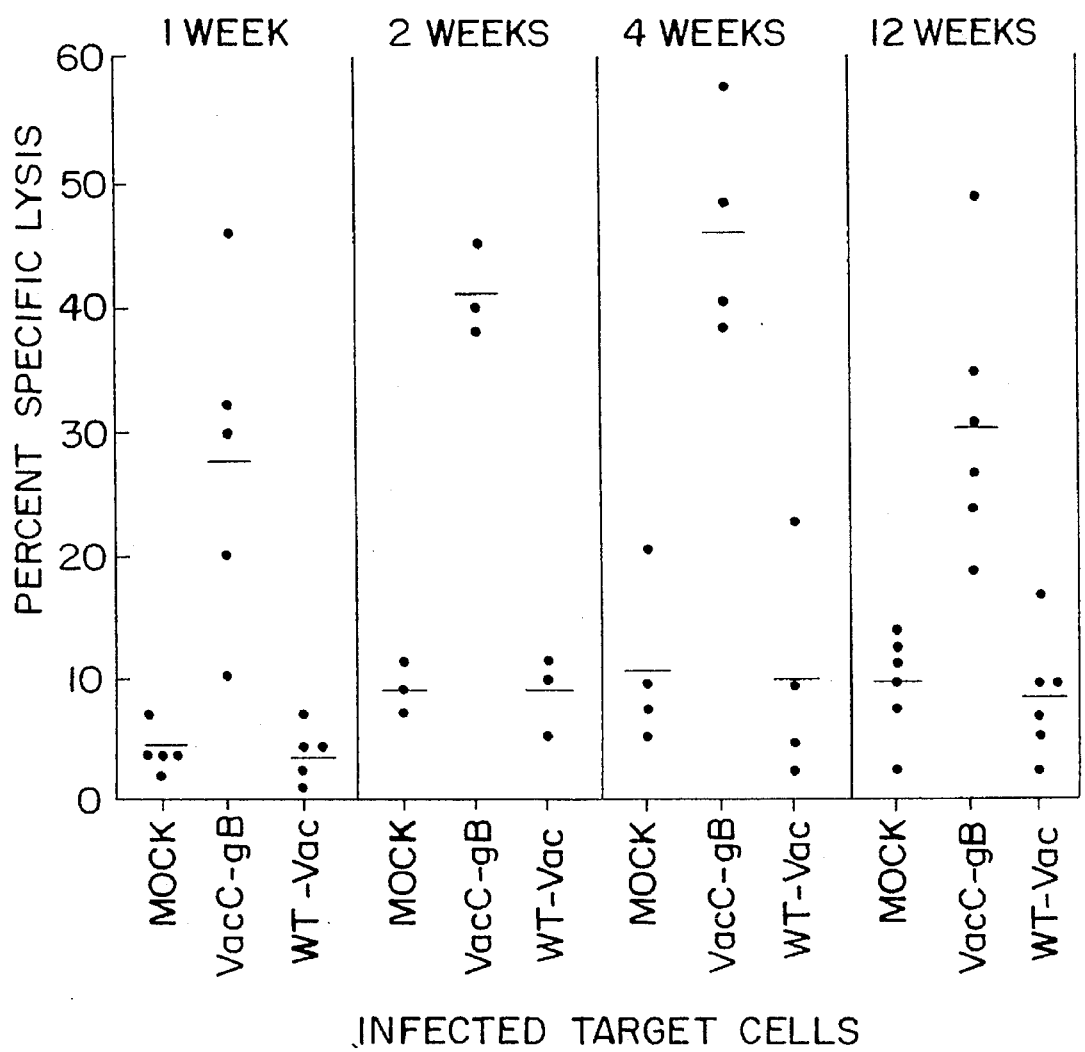

FIG. 3 illustrates the kinetics of the HCMV-gB-specific CTL response after Ad-gB immunization, described in more detail in Example 6. The dots represent results of individual mice; and horizontal bars represent means of results of individual mice.

DETAILED DESCRIPTION OF THE INVENTION

The present invention provides novel vaccine components for HCMV which comprise an adenovirus expression system capable of expressing a selected HCMV subunit gene in vivo. Alternatively the selected subunit for use in a vaccine may be expressed in, and isolated from, the recombinant adenovirus expression system.

As provided by the present invention, any adenovirus strain capable of replicating in mammalian cells in vitro may be used to construct an expression vector for the selected HCMV subunit. However, a preferred expression system involves a non-defective adenovirus strain, including, but not limited to, adenovirus type 5. Alternatively, other desirable adenovirus strains may be employed which are capable of being orally administered, for use in expressing the CMV subunit in vivo. Such strains useful for in vivo production of the subunit in addition to adenovirus-5 strains include adenovirus type 4, 7, and 21 strains. [See, e.g., Takajuji et al, cited above]. Appropriate strains of adenovirus, including those identified above and those employed in the examples below are publicly available from sources such as the American Type Culture Collection, Rockville, Md.

In the practice of one embodiment of this invention the HCMV subunit may be produced in vitro by recombinant techniques in large quantities sufficient for use in a subunit vaccine. Alternatively, the recombinant adenovirus containing the subunit may itself be employed as a vaccine component, capable of expressing the subunit in vivo.

The presently preferred subunit proteins for use in the present invention are the HCMV gB subunit and the HCMV IE-exon 4 subunit. One embodiment of the present invention provides a replication competent adenovirus-5 vector carrying the HCMV gB gene. Another embodiment of the invention provides a replication competent adenovirus-5 vector carrying the HCMV IE-exon 4 gene.

However, it is anticipated that in the construction of the adenovirus vectors of this invention, any of the subunits of the HCMV envelope protein may be employed. In a manner similar to the use of the gB or IE-exon-4 subunit in this vaccine, other subunits of CMV which may be employed in the production of a vaccine according to the invention may be selected from the gcII, gcIII, or immediate early subunits of the human virus. Alternatively, more than one HCMV subunit may be employed in a vaccine according to the teachings of the present invention.

A number of strains of human CMV have been isolated. For example, the Towne strain of CMV, a preferred strain for use in preparation of a vaccine of this invention because of its broad antigenic spectrum and its attenuation, was isolated from the urine of a two month old male infant with cytomegalic inclusion disease (symptoms—central nervous system damage and hepatosplenomegaly). This strain of CMV was isolated by Stanley A. Plotkin, M.D. of The Wistar Institute of Anatomy and Biology, Philadelphia, Pa., and is described in *J. Virol.*, 11 (6): 991 (1973). This strain is freely available from The Wistar Institute or from the ATCC under accession number VR-977. However, other strains of CMV useful in the practice of this invention may be obtained from depositories like the ATCC or from other institutes or universities.

In addition to isolating the desired subunit from an available strain of HCMV for insertion into the selected adenovirus, the sequences of the subunits of two HCMV strains have been published [See, e.g., Mach et al, *J. Gen. Virol.*, 67:1461–1467 (1986); Cranage et al, (1986) cited above; and Spaete et al, *Virol.*, 167:207–225 (1987). These subunit sequences can therefore be chemically synthesized by conventional methods known to one of skill in the art, or the sequences purchased from commercial sources.

The recombinant adenovirus of the present invention may also contain multiple copies of the HCMV subunit. Alternatively, the recombinant virus may contain more than one HCMV subunit type, so that the virus may express two or more HCMV subunits or immediate early antigens and subunits together.

In the construction of the adenovirus vector of the present invention, the CMV subunit sequence is preferably inserted in an adenovirus strain under the control of an expression control sequence in the virus itself. The adenovirus vector of the present invention preferably contains other sequences of interest in addition to the HCMV subunit. Such sequences may include regulatory sequences, enhancers, suitable promoters, secretory signal sequences and the like. The techniques employed to insert the subunit sequence into the adenovirus vector and make ether alterations in the viral DNA, e.g., to insert linker sequences and the like, are known to one of skill in the art. See, e.g., T. Maniatis et al, "Molecular Cloning. A Laboratory Manual", Cold Spring Harbor Laboratory, Cold Spring Harbor, N.Y. (1982). Thus, given the disclosures contained herein the construction of suitable adenovirus expression vectors for expression of an HCMV subunit protein is within the skill of the art. Example 1 below describes in detail the construction of a non-defective adenovirus containing the HCMV gB subunit. Example 15 below describes in detail the construction of a non-defective adenovirus containing the HCMV IE-exon-4 subunit.

The recombinant adenovirus itself, constructed as described above, may be used directly as a vaccine component. According to this embodiment of the invention, the recombinant adenovirus, containing the HCMV subunit, e.g., the gB subunit, is introduced directly into the patient by vaccination. The recombinant virus, when introduced into a patient directly, infects the patient's cells and produces the CMV subunit in the patient's cells. The inventors have found that this method of presenting these HCMV genes to a vaccinate is particularly capable of eliciting a protective immune response.

Examples 5 through 14 describe experiments demonstrating that a recombinant adenovirus of this invention, Ad-gB, containing the gB subunit is capable of producing a protective CTL response in immunized mice. Similarly Examples 16 and 17 below demonstrate the ability of the adenovirus recombinant of this invention, Ad-IE, containing subunit IE-exon-4 to elicit a CTL response from immunized mice.

The use of these adenovirus recombinants as vaccines capable of inducing a CTL response is surprising in view of the results obtained in the same assays of the examples with other known virus types, which have been used in vaccines previously. For example, the adenovirus recombinants of this invention were superior vaccinal agents, i.e., produced a potent CTL response, in contrast to vaccinia recombinants containing the same subunits, which produced a low level CTL response (see Examples 5–15 below).

According to another embodiment of this invention, once the recombinant viral vector containing the CMV subunit protein, e.g., the IE-exon 4 subunit, is constructed, it may be infected into a suitable host cell for in vitro expression. The infection of the recombinant viral vector is performed in a conventional manner. [See, Maniatis et al, supra.] Suitable host cells include mammalian cells or cell lines, e.g., A549 (human lung carcinoma) or 293 (transformed human embryonic kidney) cells.

The host cell, once infected with the recombinant virus of the present invention, is then cultured in a suitable medium, such as Minimal Essential Medium (MEM) for mammalian cells. The culture conditions are conventional for the host cell and allow the subunit, e.g., IE-exon4, to be produced either intracellularly, or secreted extracellularly into the medium. Conventional protein isolation techniques are employed to isolate the expressed subunit from the selected host cell or medium.

When expressed in vitro and isolated from culture, the subunit, e.g., IE-exon4, may then be formulated into an appropriate vaccine composition. Such compositions may generally contain one or more of the recombinant CMV subunits.

The preparation of a pharmaceutically acceptable vaccine composition, having appropriate pH, isotonicity, stability and other conventional characteristics is within the skill of the art. Thus such vaccines may optionally contain other components, such as adjuvants and/or carriers, e.g., aqueous suspensions of aluminum and magnesium hydroxides.

Thus, the present invention also includes a method of vaccinating humans against human CMV infection with the recombinant adenovirus vaccine composition. This vaccine composition is preferably orally administered, because adenoviruses are known to replicate in cells of the stomach. Previous studies with adenoviruses have shown them to be safe when administered orally [see, e.g., Collis et al, cited above]. However, the present invention is not limited by the route of administration selected for the vaccine.

When the recombinant adenovirus is administered as the vaccine, a dosage of between $10^5$ and $10^8$ plaque forming units may be used. Additional doses of the vaccines of this invention may also be administered where considered desirable by the physician. The dosage regimen involved in the method for vaccination against CMV infection with the recombinant virus of the present invention can be determined considering various clinical and environmental factors known to affect vaccine administration.

Alternatively, the vaccine composition may comprise one or more recombinantly-produced human CMV subunit proteins, preferably the IE-exon-4 subunit. The in vitro produced subunit proteins may be introduced into the patient in a vaccine composition as described above, preferably employing the oral, nasal or subcutaneous routes of administration. The presence of the subunit produced either in vivo or as part of an in vitro expressed subunit administered with a carrier, stimulates an immune response in the patient. Such an immune response is capable of providing protection against exposure to the whole human CMV microorganism. The dosage for all routes of administration of the in vitro vaccine containing one or more of the CMV subunit proteins is generally greater than 20 micrograms of protein per kg of patient body weight, and preferably between 40 and 80 micrograms of protein per kilogram.

The utility of the recombinant adenoviruses of the present invention is demonstrated through the use of a novel mouse experimental model which characterizes cytotoxic T lymphocyte (CTL) responses to individual proteins of strictly human-restricted viruses. For example, the model as used herein is based on the use of two types of recombinant viruses, an adenovirus and a canarypox virus, both expressing a gene of the same HCMV protein. This model is useful in identifying immunodominant HCMV proteins and immunodominant epitopes of individual proteins to incorporate into an appropriate immunizing vector, analysis of proteins of various HCMV strains, immunization protocols and the longevity of cell-mediated immunity to individual proteins or epitopes; and investigation of the optimal vector for effective introduction of a certain antigen or epitope to the host immune system.

According to this model, mice are immunized with one recombinant, such as that of the invention, and CTL activity tested in target cells infected with the other recombinant. Specifically, Examples 5–11 below provide a murine model of the cytotoxic T lymphocyte (CTL) response to the glycoprotein B (gB) gene of human cytomegalovirus (HCMV) based on the use of gB-expressing adenovirus (Ad-gB) and several poxvirus recombinants.

Using this model, it has been demonstrated that the human CMV subunit gB (HCMV-gB) can elicit a major histocompatibility complex (MHC) class I-restricted HCMV-gB-specific CTL response in mice. Mice of different major histocompatibility (MHC) haplotypes [CBA ($H-2^k$), BALB/k ($H-2^k$) and BALB/c ($H-2^d$)] infected with the Ad-gB recombinant developed an adenovirus specific CTL response. However only the $H-2^k$ mice demonstrated a significant HCMV-gB-specific CTL response, as indicated by the MHC class I-restricted lysis of vaccinia Copenhagen strain-gB (VacC-gB) recombinant-infected target cells by $H-2^k$ mouse immune spleen cells.

Further, of the adenovirus recombinants tested, only the recombinant adenovirus containing the gB subunit (Ad-gB) and a canarypox-gB (Cp-gB) recombinant were potent gB-specific CTL inducers in mice. Both of these recombinants elicited a significant MHC class I-restricted HCMV-gBspecific CTL response in CBA mice, whereas VacC-gB, and vaccinia WR strain (VacW-gB) recombinants elicited only a weak gB-specific CTL response in these mice, indicating that gB is an inducer of CTL in mice depending on the expression vector used for immunization. The gB-specific cytotoxicity was mediated by CD8 lymphocytes.

The following examples illustrate the construction of a non-defective adenovirus strain capable of expressing the HCMV major envelope glycoprotein subunit gB or IE-exon-4, and the efficacy of this composition as an HCMV vaccine. These examples are illustrative only and do not limit the scope of the present invention.

EXAMPLE 1

Construction of a Non-defective Adenovirus—gB (Ad-B) Recombinant

The gB gene was cloned from the Towne strain of HCMV [Wistar Institute] as follows. The gB gene was first mapped to the 20.5 kb Hind III D fragment of HCMV using oligonucleotides that corresponded to the 5' and 3' termini of the published AD-169 gB sequence [See, Cranage et al (1986), cited above]. The Hind III fragment was cut with XbaI to generate a 9.8 kb fragment. This fragment was then cut with XmaIII to generate a 3.1 kb fragment. The 3.1 kb XmaIII fragment which contained the gB gene, had XbaI linkers attached to its 5' and 3' termini.

An adenovirus type 5 plasmid, pad5 Bam-B, which contains the 59.5–100 mu region of the Ad5 adenovirus genome cloned into the BamHI site of pBR322 [See, R. L. Berkner et al, *Nucl. Acids Res.*, 11:6003–6020 (1983) and M. E. Morin et al, cited above] was digested with XbaI to remove the 78.5 mu–84.7 mu sequences of the Ad5 genome. The 78.5 to 84.7 mu deletion removes most of the coding region of the E3 transcription unit of Ad5 but leaves the E3 promoter intact. The XbaI-linked 3.1 kb fragment of CMV containing the gB gene was inserted into this XbaI site of pad5 Bam-B. FIG. 1A provides a diagrammatic illustration of the above description.

To generate recombinant virus, the 0–76 mu fragment of wild type Ad5 virus was isolated by digesting the viral DNA with EcoRI [See, U. Petterson et al, *J. Mol. Biol.*, 73:125–130 (1973)]. This fragment was cotransfected with the 59.5 to 100 mu BamHI fragment of pad5 Bam-B containing the gB gene as described above into human embryonic kidney 293 cells, available from the American Type Culture Collection. The Ad-gB recombinant was generated by overlap recombination between the viral sequences as illustrated in FIG. 1B.

The gB recombinant virus was plaque purified on human lung carcinoma A549 cells [ATCC CCL185] using standard procedures. Viruses containing both orientations of the gB gene, as determined by Southern blotting, were isolated.

The recombinant containing the gB gene in the same 5' to 3' direction as the adenovirus E3 promoter of the adenovirus type 5 strain is under the transcriptional control of the E3 promoter. The plaque purified recombinant virus retains the cloning XbaI sites. The above-described cloned gB gene is devoid of its natural promoter according to the DNA sequence of gB identified in Spaete et al, (1987), cited above.

EXAMPLE 2

Production of the gB Subunit

The adenovirus gB plasmid construct and the Ad5 mu 0–76 DNA of Example 1 were cotransfected into 293 cells, human cells transformed by adenovirus 5 early genes [See, Graham et al, *J. Gen. Virol.*, 36:59–72 (1977); and ATCC CRL1573] employing conventional procedures. This transfection generated a functional recombinant virus by homologous overlap recombination as shown in FIG. 1B.

Southern blot analysis confirmed the presence of an adenovirus, type 5, containing the HCMV gB subunit (referred to as either Ad-5/gB or Ad-gB) recombinant virus which was subsequently purified by plaque purification using standard procedures.

The recombinant virus AD-5/gB, expresses gB subunit protein as determined by conventional assays, i.e., immunofluorescence on fixed cells and by Western blot using monospecific guinea pig antiserum and monoclonal antibodies to gB protein [See, e.g., T. Maniatis et al, cited above]. The Ad-5/gB recombinant, also referred to as Ad-gB, is also described in applicant's publication [Marshall et al., *J. Infect. Dis.*, 162:1177–1181 (1990)] published after the filing date of the original parent application from which this application claims priority.

EXAMPLE 3

Recombinant Viruses used in CTL Assays

The following recombinant viruses were used in the CTL assays of Examples 4–17 below to demonstrate the vaccine utility of the recombinant adenoviruses of the present invention.

Wild-type human adenovirus type 5 (WT-Ad) and the Ad-gB recombinant were propagated in human lung carcinoma A549 cells [ATCC CCL185], as described in Example 1.

An E3-deleted adenovirus type 5 mutant lacking the XbaI D fragment of adenovirus DNA (Ad5ΔE3) was constructed by overlap recombination, using plasmid pad-5 mu 59.5–100, which was deleted in E3 sequences (mu 78.5–84) using the techniques described in Example 1, and pad-5 mu 0–75.9 [G. S. Marshall et al, *J. Infect. Dis.*, 162:1177–1181 (1990), hereby incorporated by reference].

A vaccinia virus recombinant containing the gB subunits (VacC-gB) described previously in Gonczol et al, *Vaccine*, 9:631–637 (1991) and the parental Copenhagen strain of vaccinia, VC-2 (also known as wild-type vaccinia (WT-Vac)) were grown in Vero cells [E. Gonczol et al, *Vaccine*, 8:130–136 (1990); J. Tartaglia et al, *Crit. Rev. Immunol.*, 10:13–30 (1990)].

The vaccinia WR strain [obtained from Dr. Enzo Paoletti, Virogenetics Corp, Troy, N.Y.] was used to develop a recombinant expressing HCMV-gB ((VacW)-gB). This recombinant was derived using a strategy similar to that described for the VacC-gB recombinant (Gonczol et al., cited above).

A canarypox recombinant [ALVAC-CMV (vCP139) which is subsequently referred to as Cp-gB] expressing the HCMV-gB gene was constructed using a strategy similar to that described for a canarypox-rabies recombinant in Taylor et al., *Vaccine* 9:190–193 (1991) [also obtained from Dr. Enzo Paoletti]. Briefly, the gene encoding the HCMV (Towne strain) glycoprotein B was inserted into a canarypox donor plasmid consisting of a polylinker flanked by genomic sequence from which a nonessential gene was specifically deleted (at a unique EcoRI site within a 3.3 kbp PvuII subgenomic fragment of canarypox DNA). Expression of the gB protein gene was placed under the transcriptional control of an early/late vaccinia virus promoter (H6) previously described [Percus et al., *J. Virol.*, 63:3829–3835 (1989)]. Cp-gB was derived and plaque-purified by standard methods [Panicali and Paoletti, *Proc. Natl. Acad. Sci. USA*, 79:4927–4931 (1982)]. The Cp-gB recombinant and parental canarypox virus (WT-Cp) were propagated on primary chick embryo fibroblasts.

EXAMPLE 4

Expression of the gB Protein in Cp-gB Recombinant Virus

Chicken embryo fibroblast (CEF) cells [ATCC CRL 1590] infected with either Cp-gB or with the parental wild-type canarypox (WT-Cp) virus preparations were analyzed by Western blot assay using the 4A guinea-pig serum directed against the gB protein. Western blot assays and the 4A guinea-pig serum, used as gB-specific antibody, were described previously in Gonczol et al., *J. Virol.*, 58:661–664 (1986). Uninfected and HCMV-infected MRC-5 cell [ATCC CCL 171] lysates were included as controls.

A diffuse band at the 140 kDa position and a double band of 55 and 58 kDa were detected in both Cp-gB-infected CEF cells and in HCMV-infected MRC-5 cells. The presence of these gB-specific proteins presumably representing the glycosylated 140 kDa precursor and the differentially glycosylated cleavage products (55 and 58 kDa) indicates that the Cp-gB recombinant expresses the inserted gB gene. The slight difference between the mobility of 55 and 58 kDa cleavage products of control and recombinant gB may reflect different glycosylation patterns.

EXAMPLE 5

Murine Model—CTL Assay

For immunization of mice, Ad-gB and WT-Ad were purified by CsCl gradient centrifugation. VacC-gB, VacW-gB and WT-Vac were purified by sucrose gradient centrifugation, and Cp-gB and WT-Cp were concentrated on sucrose cushion.

Six- to 8-week-old female BALB/c and CBA mice (from Harlan Sprague-Dawley and Jackson) and 12-week-old male BALB/k mice (from The Wistar Institute Animal Facility) were immunized intraperitoneally (i.p.) with the recombinant viruses described above at $1-5\times10^8$ pfu unless otherwise stated.

One to 12 weeks later, spleens were aseptically removed and cell suspensions were prepared by gently pressing the spleens through a stainless steel mesh. Cells were suspended at $2.5\times10^6$ viable cells/ml in RPMI 1640 medium containing 5% FBS (Gibco), $2\times10^{-5}$M 2-mercaptoethanol, 14 mM HEPES buffer, glutamine and 50 µg/ml gentamicin. Spleen cell cultures were restimulated in vitro with Ad-gB (multiplicity of infection (m.o.i.)=10) or VacC-gB (m.o.i.=0.5) infected autologous spleen cells for 5 days in 24-well plates. Cytolytic activity of nonadherent spleen cells was tested in a chromium release assay which was performed as follows.

A. T-cell Subset Depletion

For in vitro depletion of CD4 or CD8 cells, $3\times10^6$ spleen cells were incubated with anti-mouse CD4 monoclonal antibody (MAb) [Pharmingen; Cat.3:01061 D; 20 µg/$3\times10^6$ cells] or CD8 MAb [Accurate; Cat.#:CL-8921; diluted 1:4] for 60 minutes at 4° C., and further incubated in the presence of rabbit complement [Accurate; Low-tox M; diluted 1:10] for 30 minutes at 37° C. The cells were washed twice and used as effector cells in a $^{51}$Cr-release test.

B. Chromium Release Assay

P815 ($H-2^d$) [ATCC TIB 64], mouse MC57 ($H-2^b$) cells [also termed MC-57G, D. P. Aden et al, *Immunogenetics*, 3:209–221 (1976)] and mouse NCTC clone 929 ($H-2^k$) cells [ATCC CCL 1] were used as target cells. The HCMV neutralization titer of mouse sera was determined on MRC-5 cells [ATCC CCL 171] by the microneutralization method as described in Gonczol et al., *J. Virol. Methods*, 14:37–41 (1986).

The target cells were infected with Ad-gB or Ad-5ΔE3 (multiplicity of infection (m.o.i.)=40–80, 40 hours) or with Vac-gB or WT-Vac (m.o.i.=5–10, 4 hours). Target cells were washed in the modified RPMI 1640 medium described above and $2\times10^6$ cells were labeled with 100 µCi of [$^{51}$Cr] NaCrO4 [Amersham, specific activity 250–500 mCi/mg] for 1 hour. The labeled target cells were washed 3 times in phosphate-buffered saline (PBS) and then mixed with the effector cells at various effector:target ratios in triplicate using 96-well U-bottomed microtiter plates and incubated for 4 hours.

Percentage specific $^{51}$Cr release was calculated as: [(cpm experimental release–cpm spontaneous release)/(cpm maximal release–cpm spontaneous release)]×100. Standard deviation of the mean of triplicate cultures was less than 10%, and spontaneous release was always less than 25%.

This CTL assay is a system in which two types of viral expression vectors, poxvirus and adenovirus, carrying the same HCMV-gB gene, are alternately used for immunization of animal or for infection of target cells to show that HCMV-gB is an inducer of CTL in mice. Using this model system, the relative immunogenicity of the gB antigen expressed by different recombinant viruses has been evaluated. Results from the repeated performance of this assay are provided in Examples 6–11 which follow.

EXAMPLE 6

MHC Class I-Restricted HCMV-gB Specific CTL in Ad-gB-immunized CBA Mice

Performance of the CTL assay of Example 5 resulted in the ability of in vitro restimulated spleen cells from CBA mice immunized i.p. with Ad-gB (FIG. 2A) or WT-Ad (FIG. 2B) to produce HCMV-gB-specific CTL response and lyse the various target cells. In the graphs of FIG. 2A and 2B, the closed squares indicate uninfected cells; closed circles indicate Ad-5 E3-infected cells; open circles indicate VacC-gB-infected cells; and delta indicates WT-Vac infected cells. In the graphs, a solid line connecting the above symbols indicates that the target cells were L-929 cells. A dotted line connecting the symbols indicates that the target cells were MC57 cells.

Assay of the ability of in vitro restimulated spleen cells from CBA mice immunized with Ad-gB or WT-Ad to lyse various target cells revealed no significant lysis of uninfected (closed squares, solid line) or WT-Vac-infected MHC-matched L-929 ($H-2^k$) cells (delta, solid line) by lymphocytes of either group of mice. However, lysis of Ad-5ΔE3-infected L-929 cells (closed circles, solid line) by these lymphocytes did occur.

For spleen cells of Ad-gB-immunized mice (FIG. 2A), gB specific lysis of VacC-gB-infected L-929 target cells (open circle, solid line) was 37, 36, 26, and 22% higher than that of WT-Vac-infected target cells (delta, solid line) at E:T ratios of 50:1, 25:1, 12.5:1 and 6:1, respectively. Vac-gB-infected MHC-mismatched ($H-2^b$) MC57 target cells (open circle, dotted line) were not lysed by the splenocytes of Ad-gB-immunized mice.

Mice immunized with WT-Ad (FIG. 2B) exhibited no gB-specific lysis of these target cells. Spleen cells of non-immunized mice restimulated in vitro with Ad-gB showed no Ad-specific or gB-specific cytotoxicity.

Thus, Ad-gB-infected CBA mice generated not only adenovirus-specific CTL, but also CTL that specifically recognize the gB protein expressed by VacC-gB in an MHC class I-restricted manner.

FIG. 3 shows the kinetics of the gB-specific CTL response. HCMV-gB-specific CTL were present 1 week after immunization and remained detectable throughout the 12-week test period, indicating the presence of gB-specific memory CTL.

EXAMPLE 7

Influence of MHC Haplotype on gB-specific CTL Response

Congenic BALB/c and BALB/k mice, which differ only in MHC haplotype, were inoculated i.p. with Ad-gB. Three weeks later spleen cells were stimulated for 5 days with Ad-gB-infected autologous spleen cells. These cells were then used as effectors in CTL assays using P815 ($H-2^d$) and L929 ($H-2^k$) as target cells. Table 1 provides the results.

TABLE 1

Induction of HCMV-gB-specific CTL Response in BALB/k but not in BALB/c mice by the Ad-gB Recombinant Virus

| Target Cells | Virus Infection of Target Cells | Effector Spleen Cells | E:T Ratio | Specific $^{51}$Cr Release (%) |
|---|---|---|---|---|
| L-929(H-2k) | — | BALB/k | 50:1 | 15 |
| | | | 25:1 | 9 |
| | | | 12.5:1 | 5 |
| | | | 6:1 | 5 |
| | Ad5 E3 | | 50:1 | 45 |
| | | | 25:1 | 33 |
| | | | 12.5:1 | 23 |
| | | | 6:1 | 14 |
| | VacC-gB | | 50:1 | 47 |
| | | | 25:1 | 33 |
| | | | 12.5:1 | 21 |
| | | | 6:1 | 13 |
| | WT-Vac | | 50:1 | 13 |
| | | | 25:1 | 8 |
| | | | 12.5:1 | 7 |
| | | | 6:1 | 4 |
| P815(H-2d) | — | BALB/c | 50:1 | 21 |
| | | | 25:1 | 13 |
| | | | 12.5:1 | 7 |
| | | | 6:1 | 5 |
| | Ad5 E3 | | 50:1 | 56 |
| | | | 25:1 | 56 |
| | | | 12.5:1 | 43 |
| | | | 6:1 | 24 |
| | VacC-gB | | 50:1 | 16 |
| | | | 25:1 | 14 |
| | | | 12.5:1 | 8 |
| | | | 6:1 | 6 |
| | WT-Vac | | 50:1 | 14 |
| | | | 25:1 | 11 |
| | | | 12.5:1 | 6 |
| | | | 6:1 | |

Adenovirus-specific lysis was elicited by the spleen cells of both mouse strains. However, a HCMV-gB specific response was observed only in Ad-gB-immunized BALB/k mice. VacC-gB-infected target cells, but not WT-Vac-infected L-929 cells, were specifically lysed. No gB-specific CTL response was observed in BALB/c mice, demonstrating that $H-2^k$ but not $H-2^d$ mice recognize the gB antigen.

EXAMPLE 8

CTL Response in CBA Mice Immunized with the VacC-gB Recombinant

Spleen cell cultures derived from CBA mice immunized i.p. with Vac-gB, were restimulated in vitro with VacC-gB-infected autologous spleen cells for 5 days and tested for cytolytic activity on Ad-5ΔE3-, Ad-gB- and WT-Vac-infected MHC-matched L-929 target cells. The results of this study are provided in Table 2 below.

TABLE 2

HCMV-gB-specific CTL Response of CBA Mice Immunized with VacC-gB

| Time after Immuni-zation | Mouse No. | E:T Ratio | Specific lysis of target cells (%) | | | |
|---|---|---|---|---|---|---|
| | | | Mock | WT-Vac | Ad-gB | Ad5ΔE3 |
| 2 weeks | 1 | 50:1 | 27 | 82 | 35 | 23 |
| | | 25:1 | 20 | 83 | 32 | 20 |
| | | 12.5:1 | 11 | 82 | 16 | 10 |
| | | 6:1 | 5 | 68 | 9 | 7 |
| | 2 | 50:1 | 11 | 87 | 14 | 7 |
| | | 25:1 | 8 | 88 | 11 | 7 |
| | | 12.5:1 | 4 | 78 | 6 | 7 |
| | | 6:1 | 3 | 68 | 5 | 4 |
| | 3 | 50:1 | 20 | 97 | 33 | 16 |
| | | 25:1 | 17 | 100 | 27 | 11 |
| | | 12.5:1 | 10 | 98 | 18 | 8 |
| | | 6:1 | 5 | 84 | 9 | 8 |
| 4 weeks | 4 | 50:1 | 20 | 83 | 36 | 25 |
| | | 25:1 | 19 | 82 | 27 | 17 |
| | | 12.5:1 | 10 | 79 | 15 | 11 |
| | | 6:1 | 4 | 72 | 10 | 7 |
| | 5 | 50:1 | 32 | 88 | 34 | 31 |
| | | 25:1 | 16 | 81 | 29 | 24 |
| | | 12.5:1 | 16 | 72 | 19 | 15 |
| | | 6:1 | 11 | 61 | 10 | 11 |
| | 6 | 50:1 | 26 | 84 | 36 | 25 |
| | | 25:1 | 19 | 80 | 28 | 19 |
| | | 12.5:1 | 13 | 85 | 15 | 11 |
| | | 6:1 | 7 | 76 | 9 | 12 |

The small difference between the percent specific lysis of Ad-gB-infected and of Ad-5ΔE3-infected target cells indicated a very low gB-specific CTL response. The vaccinia virus specific CTL response was very high in all vaccinia-gB immunized mice, indicating effective expression of vaccinia virus proteins in these animals.

EXAMPLE 9

Induction of HCMV-gB-specific CTL Response in CD-gB inoculated CBA mice

The potent gB-specific CTL response generated by the Ad-gB recombinant was compared with the response induced by immunization of CBA mice with the Cp-gB recombinant (described in Example 4), because of its relative potent immunogenicity [Taylor et al., *Virology*, 187:321–328 (1991)].

Mice were immunized i.p. with $2 \times 10^8$ Cp-gB recombinant virus, sacrificed 2–4 weeks later and spleen cell cultures were restimulated in vitro with VacC-gB-infected autologous spleen cells for 5 days. The lytic effect of lymphocytes was tested on uninfected, Ad-gB-, and Ad-5ΔE3-infected MHC matched L-929 and MHC mismatched MC-57 target cells in a 4-hour $^{51}$Cr release assay.

Table 3 shows the results obtained by using the L-929 target cells.

TABLE 3

HCMV-gB-specific CTL Response of CBA Mice Immunized with Cp-gB

| Time after Immunization | Mouse No. | E:T Ratio | Specific lysis of target cells (%) | | | | |
|---|---|---|---|---|---|---|---|
| | | | Mock | Ad-gB | Ad5 E3 | Vac-gB | Wt-Vac |
| 2 weeks | 1 | 50:1 | 26 | 57 | 22 | 50 | 24 |
| | | 25:1 | 24 | 50 | 19 | 42 | 21 |
| | | 12.5:1 | 13 | 31 | 13 | 31 | 12 |
| | | 6:1 | 6 | 18 | 7 | 18 | 7 |
| | 2 | 50:1 | 9 | 74 | 10 | 70 | 16 |
| | | 25:1 | 9 | 59 | 7 | 60 | 10 |
| | | 12.5:1 | 3 | 48 | 5 | 50 | 5 |
| | | 6:1 | 2 | 37 | 2 | 28 | 3 |
| 3 weeks | 3 | 50:1 | 13 | 55 | 10 | 90 | 24 |
| | | 25:1 | 11 | 47 | 7 | 81 | 19 |
| | | 12.5:1 | 4 | 32 | 6 | 66 | 11 |
| | | 6:1 | 2 | 24 | 3 | 44 | 7 |
| | 4 | 50:1 | 20 | 61 | 12 | 98 | 39 |
| | | 25:1 | 15 | 56 | 11 | 90 | 31 |
| | | 12.5:1 | 6 | 44 | 7 | 78 | 20 |
| | | 6:1 | 3 | 33 | 4 | 58 | 12 |
| 4 weeks | 5 | 50:1 | 30 | 76 | 23 | 82 | 55 |
| | | 25:1 | 22 | 74 | 16 | 81 | 48 |
| | | 12.5:1 | 9 | 59 | 9 | 60 | 32 |
| | | 6:1 | 10 | 43 | 6 | 60 | 23 |
| | 6 | 50:1 | 16 | 87 | 12 | 81 | 46 |
| | | 25:1 | 10 | 83 | 10 | 76 | 33 |
| | | 12.5:1 | 5 | 54 | 7 | 67 | 24 |
| | | 6:1 | 1 | 44 | 5 | 49 | 15 |

MC57 target cells infected with either Ad-gB or VacC-gB recombinant were not specifically lysed (% lysis <10% at any combination of effector:target cells). At all E:T ratios tested, each mouse demonstrated relatively high gB-specific lysis of L-929 target cells. Thus the Cp-gB recombinant, like the Ad-gB recombinant, elicited a potent MHC class I-restricted gB-specific CTL response.

EXAMPLE 10

Relative Potency of Ad-gB, Cp-gB and VacC-gB in the Induction of CTL Response in CBA Mice CBA mice were immunized i.p. with $1\times10^8$ pfu of Ad-gB, Cp-gB or VacC-gB on the same day. Two weeks later spleen cells of two mice of each group were pooled, divided in half and restimulated in vitro for five days with either VacC-gB or Ad-gB. The lytic effect of cells on Ad-gB-, Ad5ΔE3-, VacC-gB- and WT-Vac-infected MHC class I-matched L-929 and MHC mismatched MC57 target cells (Table 4) was tested in the 4-hour $^{51}$Cr release assay on the same days.

TABLE 4

Comparative Ability of Cp-gB, Ad-gB and VacC-gB to Induce HCMV-gB-specific CTL Response in CBA Mice

| Mice Immunized With | in vitro restim. with | Target Cells | E:T Ratio | Specific lysis of target cells (%) | | | |
|---|---|---|---|---|---|---|---|
| | | | | Ad-gB | AdΔE3 | VacC-gB | WT-Vac |
| Cp-gB | Ad-gB | L-929 | 40:1 | 48 | 10 | 28 | 7 |
| | | | 20:1 | 29 | 8 | 25 | 5 |
| | | | 10:1 | 16 | 2 | 11 | 2 |
| | | | 5:1 | 11 | 1 | 6 | 3 |
| | VacC-gB | | 40:1 | 44 | 10 | 35 | 11 |
| | | | 20:1 | 28 | 6 | 24 | 7 |
| | | | 10:1 | 16 | 3 | 13 | 3 |
| | | | 5:1 | 10 | 1 | 8 | 2 |
| | Ad-gB | MC57 | 40:1 | 1 | 1 | 2 | 3 |
| | VacC-gB | | 40:1 | 2 | 1 | 4 | 3 |
| Ad-gB | Ad-gB | L-929 | 40:1 | 75 | 56 | 34 | 8 |
| | | | 20:1 | 56 | 36 | 24 | 6 |
| | | | 10:1 | 32 | 20 | 14 | 3 |
| | | | 5:1 | 19 | 10 | 8 | 1 |
| | VacC-gB | | 40:1 | 69 | 5 | 53 | 5 |
| | | | 20:1 | 47 | 3 | 35 | 4 |
| | | | 10:1 | 25 | 1 | 20 | 3 |
| | | | 5:1 | 15 | 1 | 12 | 1 |
| | Ad-gB | MC57 | 40:1 | 3 | 2 | 4 | 5 |
| | VacC-gB | | 40:1 | 1 | 1 | 1 | 3 |

TABLE 4-continued

Comparative Ability of Cp-gB, Ad-gB and VacC-gB to Induce
HCMV-gB-specific CTL Response in CBA Mice

| Mice Immunized With | in vitro restim. with | Target Cells | E:T Ratio | Specific lysis of target cells (%) | | | |
|---|---|---|---|---|---|---|---|
| | | | | Ad-gB | AdΔE3 | VacC-gB | WT-Vac |
| VacC-gB | Ad-gB | L-929 | 40:1 | 15 | 9 | 10 | 8 |
| | | | 20:1 | 8 | 6 | 5 | 6 |
| | | | 10:1 | 4 | 3 | 4 | 3 |
| | | | 5:1 | 3 | 1 | 3 | 2 |
| | VacC-gB | | 40:1 | 9 | 5 | 74 | 88 |
| | | | 20:1 | 7 | 3 | 62 | 72 |
| | | | 10:1 | 4 | 1 | 43 | 53 |
| | | | 5:1 | 1 | 1 | 28 | 33 |
| | Ad-gB | MC57 | 40:1 | 1 | 1 | 2 | 3 |
| | VacC-gB | | 40:1 | 3 | 1 | 1 | 4 |

Spleen cells of Ad-gB- and Cp-gB-immunized mice exhibited a significant HCMV-gB-specific cytolytic activity, regardless of the virus used for in vitro restimulation and for target cell infection, whereas the CTL response observed after VacC-gB immunization was very low. These results indicate that the low CTL response associated with VacC-gB does not reflect suboptimal experimental conditions.

To examine the possibility that the low gB-specific CTL response of VacC-gB-infected mice reflects poor expression of gB in CBA mice immunized i.p. with $1-2 \times 10^8$ pfu of the different recombinant viruses, the following study was performed. Four to 10 weeks after immunization, mice were sacrificed and blood was taken by cardiac puncture on the day of initiation of spleen cell cultures and sera was tested for HCMV neutralizing activity. Spleen cells were restimulated with Vac-gB or Ad-gB, and gB-specific CTL activity of spleen cells was determined.

HCMV-gB-specific percent lysis was calculated as: (% lysis of MHC class i matched gB-recombinant-infected target cells−% lysis of parental virus-infected target cells). VacW-gB-immunized mice were also included in these experiments, because preliminary experiments indicated that the VacW-gB recombinant induced a high HCMV neutralizing antibody response in CBA mice. Parental viruses did not induce HCMV-neutralizing antibodies or gB-specific CTL responses.

Table 5 summarizes the results of recombinant immunized mice.

TABLE 5

HCMV-gB-specific CTL Activity of Spleen
Cells and HCMV-specific Neutralizing Antibody in
Sera of Individual Mice Immunized with
Ad-gB, Cp-gB, VacC-gB or VacW-gB

| Immunization With | Mouse No. | gB-specific CTL (% lysis) | Antibody Titer |
|---|---|---|---|
| Ad-gB | 1 | 16 | 1:64 |
| | 2 | 40 | 1:12 |
| | 3 | 47 | 1:64 |
| | 4 | 44 | 1:96 |
| Cp-gB | 5 | 16 | 1:128 |
| | 6 | 31 | 1:128 |
| | 7 | 66 | 1:64 |
| | 8 | 72 | 1:128 |
| VacC-gB | 9 | 1 | 1:64 |
| | 10 | 1 | 1:96 |
| | 11 | 12 | 1:48 |
| | 12 | 7 | 1:64 |
| | 13 | 4 | 1:32 |
| VacW-gB | 14 | 1 | 1:192 |
| | 15 | 1 | 1:256 |
| | 16 | 21 | 1:64 |
| | 17 | 14 | 1:16 |
| | 18 | 6 | 1:32 |

HCMV neutralizing antibody was detected in each serum sample obtained from mice immunized with the different recombinant viruses. Ad-gB and Cp-gB induced significant CTL response with individual differences (16 to 72% gB-specific lysis). VacC-gB and VacW-gB-immunized mice demonstrated poor or no CTL activity. Mice (no. 16, 17 and 18) immunized with a lower dose of VacW-gB ($2 \times 10^7$ pfu) showed some gB-specific CTL activity, raising the possibility that the $2 \times 10^8$ pfu of VacC-gB was too high to obtain an optimal CTL response.

However, in subsequent experiments spleen cells from CBA mice immunized with $1 \times 10^7$ or $5 \times 10^7$ pfu of VacC-gB exhibited no gB-specificity at all, demonstrating that high immunizing virus dose does not determine the poor CTL response.

EXAMPLE 11

Characterization of Cells Responsible for
HCMV-gB Specific Cytotoxic Activity

MHC class I restriction of the anti-gB cytotoxic activity provided evidence that CTL were present in the spleens of Ad-gB or Cp-gB-immunized mice. CBA mice were immunized i.p. with $1 \times 10^8$ pfu of Ad-gB, sacrificed 2 weeks later, and spleen cells restimulated in vitro with VacC-gB (experiment I). In experiment II, CBA mice were immunized i.p. with $2 \times 10^8$ pfu of Cp-gB, 8 weeks later spleen cells isolated from two mice were pooled and one part of the cell pool restimulated in vitro with Ad-gB, and the other part with VacC-gB.

To characterize further the cells responsible for anti-gB cytotoxicity, in vitro restimulated spleen cells of Ad-gB-immunized or Cp-gB-immunized mice were depleted in vitro with an anti-CD8 or anti-CD4 MAb and complement prior to the addition of $^{51}$Cr-labeled H-2-matched targets. Anti-gB activity was inhibited almost completely by treatment with anti-CD8 MAb, whereas no effect was seen using anti-CD4 MAb (Table 6). Thus the CD8 lymphocyte subset mediates the gB-specific lysis of the target cells.

cited above, and Hjorth et al, *Arch. Virol.*, 100:279–283 (1988). Briefly described, hamsters are inoculated intranasally with $10^7$ to $10^8$ pfu of Ad-5/gB recombinant virus and evaluated for production of immunity to HCMV. The inoculated animals demonstrate immunity to HCMV by the

TABLE 6

Phenotype of HCMV-gB-specific CTL

| Immunization | Restimulation | Treatment of Spleen Cells | Specific lysis of Target cells (%) | | |
|---|---|---|---|---|---|
| | | | VacC-gB | WT-Vac | Mock |
| Experiment I | | | | | |
| Ad-gB | VacC-gB | — | 40 | 3 | ND |
| | | C' | 35 | 4 | ND |
| | | anti-CD4 | 36 | 4 | ND |
| | | anti-CD4 + C' | 37 | 4 | ND |
| | | anti-CD8 | 36 | 4 | ND |
| | | anti-CD8 + C' | 6 | 3 | ND |
| Experiment II | | | | | |
| Cp-gB | VacC-gB | — | 69 | 23 | 10 |
| | | C' | 68 | 25 | 12 |
| | | anti-CD4 | 67 | 22 | 11 |
| | | anti-CD4 + C' | 66 | 24 | 7 |
| | | anti-CD8 | 68 | 23 | 10 |
| | | anti-CD8 + C' | 11 | 7 | 5 |
| | Ad-gB | — | 64 | 10 | 10 |
| | | C' | 68 | 11 | 12 |
| | | anti-CD4 | 58 | 10 | 10 |
| | | anti-CD4 + C' | 65 | 9 | 11 |
| | | anti-CD8 | 61 | 10 | 7 |
| | | anti-CD8 + C' | 10 | 5 | 3 |

EXAMPLE 12

Induction of HCMV-specific Neutralizing Antibody and Helper T Cell Responses with gB Recombinant Hamsters and guinea pigs inoculated intranasally (i.n.), and mice inoculated intraperitoneally (i.p.), per os (p.o.) or i.n. with live Ad-gB recombinant virus prepared according to Example 1 above developed anti-HCMV neutralizing antibodies. Briefly, hamsters, guinea pigs and mice were inoculated with $10^8$–$10^9$ p.f.u. of Ad-gB recombinant virus by i.p. or i.n. or i.p. or p.o. route of immunization. Serum samples obtained at 2–20 weeks after inoculation were tested in a microneutralization assay described in Gonczol et al, *J. Virol. Meth.*, 14:37–41 (1986). All animals developed HCMV-neutralizing antibodies at a serum dilution of 1:8 to 1:256.

Spleen cells of BALB/c and CBA mice inoculated i.p., i.n., or p.o. with the Ad-gB recombinant showed a gB specific in vitro lymphocyte proliferation (LP) response [stimulation index (SI) 5], when HCMV is used for in vitro stimulation of lymphocytes.

These results show that the HCMV-gB protein, expressed by an adenovirus vector in vivo, can prime T cells that are specifically responsive to the gB protein expressed by HCMV. [See, Berencsi et al, in *Progress in Cytomegalovirus Research*, pp 191–194 (1991), ed. M. P. Landini].

EXAMPLE 13

Immunization Experiments with Ad-5/gB Recombinant

Immunization experiments were performed with the vaccine composition of Example 2 using a Syrian hamster model of adenovirus infection as described in Morin et al, production of neutralizing antibody to HCMV as detected by a plaque reduction neutralization assay according to J. L. Waner et al, in "Manual of Clinical Immunology", eds. N. E. Rose and H. Friedman, American Society for Microbiology, Washington, D.C., pp. 473–477 (1976).

Immunization of human subjects with the live recombinant virus are performed according to the protocol described essentially in I. H. Top et al, *J. Infect. Dis.*, 124:155–160 (1971). The vaccine of this invention is expected to provide analogous results in humans as in the hamster model, i.e., the production of neutralizing antibody to HCMV.

EXAMPLE 14

Protection of Ad-gB Immunized Mice

A T cell mediated protective effect of gB protein, as presented by the Ad-gB virus of Example 2, was shown by demonstrating a gB specific protection of Ad-gB-immunized mice from a lethal dose of a vaccinia-gB recombinant virus using the model of Example 5.

CBA mice were immunized intraperitoneally (i.p.) or per os with the Ad-gB recombinant virus and 5–18 days later challenged intracerebrally (i.c.) with a lethal dose of a vaccinia-gB recombinant virus (WR-strain of vaccinia, which is neurovirulent for mice). Another group of mice were immunized i.p. with the Ad-gB virus and challenged 5 days later with the WR-gB vaccinia recombinant virus, inoculated intranasally (i.n.).

92% of the Ad-gB immunized mice (i.p. route of immunization, a group of 100 mice) were protected from the lethal dose of the WR-gB challenge, inoculated i.c. 95% of the Ad-gB immunized mice (per os route of immunization, a group of 30 mice) were also protected from the lethal dose of the WR-gB i.c. challenge. Further, the replication of the WR-gB virus in the lungs, following i.n. challenge, was inhibited in the Ad-gB-immune mice (i.p. route of immunization), as compared with the replication of the parental WR-vaccinia strain, as detected by infectious virus titration of the lungs. Three groups of control mice (30 mice in each group), immunized i.p. with wild type adenovirus-5, or an adenovirus-5 with a deletion in the E3 region, or an adenovirus-5 recombinant with a HCMV-immediate-early gene insert, were not protected from the WR-gB i.c. challenge (99% of these mice died). Two other control groups of mice (30 mice in each group), were immunized i.p. with the Ad-gB virus and then challenged i.c. either with the parental WR-vaccinia-strain, or a WR-vaccinia recombinant carrying the HCMV-immediate-early gene insert: all mice died from the challenge viruses. These results showed the gB-specificity of the protection.

Nude and SCID mice (20 animals in each group), immunized i.p. with Ad-gB and challenged i.c. with the WR-gB recombinant, were not protected, indicating that immune mechanism(s) is responsible for the protection. Non-immune CBA mice, inoculated intravenously (i.v.) with splenic T cells of Ad-gB mice then challenged i.c. with the WR-gB virus, were protected, suggesting that gB-specific immune T cells are involved in the protection.

EXAMPLE 15

Construction of Ad-IE exon-4 Recombinant Virus

The protection of humans from CMV infection or virus-induced diseases is based on antibody dependent and/or T-cell dependent immune responses. The following experimental data demonstrates that an adenovirus recombinant containing the major immediate early (IE) gene of HCMV elicits a protective immune response in mice.

To construct the IE-exon-4 adenovirus recombinant, the polymerase chain reaction (PCR) technique was used to amplify the exon 4 portion of the IE gene. The PCR primers were synthesized so as to incorporate the proper restriction endonuclease cleavage site (XbaI) for insertion into the XbaI site of the adenovirus vector. In addition, the 3' primers were engineered so that the Exon 4 protein contained a termination signal. A XbaI E fragment of HCMV (Towne strain) was used as an Exon 4 gene template for the PCR reaction. In this construct the E3 coding region (between map units 78.5 and 84.0) of the adenovirus is replaced by the exon-4 fragment.

The exon-4 product of the HCMV-IE gene was shown to be a target for CD8 cytotoxic and CD4 lymphoproliferative T cell responses in humans [Alp et al, *J. Virol.*, 65:4812 (1991), incorporated by reference]. The Ad-IE exon-4 construct is non-defective in replication (i.e., capable of replicating normally) in tissue culture cells.

This Ad-IE exon-4 recombinant was used in the in vitro cytotoxic T lymphocyte (CTL) assay and mouse model described above.

EXAMPLE 16

CTL Response of Ad-IE exon-4 Recombinant

The CTL-assay was carried out as described in Example 5. In this CTL assay mice were immunized with Ad-IE-exon-4 recombinant virus and target cells were infected with Vac(WR strain)-IE recombinant virus or parental vaccinia virus. Briefly, mice were immunized i.p. with Ad-gB at $1-2\times10^8$ p.f.u. These spleen cell cultures were restimulated in vitro with Ad-gB or Vaccinia (Copenhagen strain)-gB (Vac-gB)-infected autologous spleen cells for 5 days. Cytolytic activity of non-adherent spleen cells was tested in a chromium release assay. The vaccinia recombinants were provided by Dr. Paoletti, Virogenetics Corporation, Troy, N.Y.

For the chromium release assay, MHC class-I matched and mismatched target cells were infected with Ad-gB, or parental adenovirus, or with Vac-gB or parental vaccinia virus. Percentage specific $^{31}$chromium release was calculated as :[(cpm experimental release-cpm spontaneous release)/(cpm maximal release-cpm spontaneous release)]× 100.

When the assay described above was performed using gB recombinants, CBA and BALB/k mice (MHC haplotype $H-2^k$) exhibited a HCMV-gB specific MHC class I restricted CTL activity. Thus, Ad-gB recombinant inoculated CBA mice and BALB/k mice generated CTL specific for the gB-protein, encoded by the inserted gene.

When tested in the CTL assay described above, the CBA mice immunized with the Ad-IE-exon-4 recombinant developed a HCMV-IE-exon-4 specific cytotoxic T cell response.

EXAMPLE 17

Protection Study using Ad-IE Exon-4

HCMV-protein-specific protection was demonstrated in Ad-HCMV immunized mice from a vaccinia-HCMV recombinant-induced encephalitis/meningitis and death, as follows. The model is described above.

In this experiment, CBA mice were immunized i.p. with $2\times10^8$ p.f.u. of the Ad-HCMV subunit protein recombinant virus, e.g. Ad-IE-exon 4 of Example 15 or Ad-gB of Example 2, and 5–18 days later were challenged intracerebrally (i.c.) with a lethal dose of a vaccinia(WR strain)-HCMV recombinant virus (e.g. Vac(WR)-gB). Vaccinia(WR strain)-IE or vaccinia(WR strain)-gB recombinant viruses were obtained from Dr. Paoletti, Virogenetics Corporation, Troy, N.Y. The WR-strain of vaccinia is neurovirulent for mice.

When tested in this mouse model, CBA mice immunized with the Ad-IE-exon-4 recombinant were protected against a lethal dose of vacciniaWR-IE recombinant virus. The protection was HCMV-IE protein specific. Ninety percent of CBA mice, immunized i.p. with Ad-IE-exon-4 recombinant virus were protected against a lethal dose of Vac(WR-strain)-IE recombinant virus, inoculated intracerebrally. Control mice, immunized with Ad-gB recombinant virus or parental adenovirus and challenged later with the Vac(WR)-IE recombinant, died within 7 days after challenge, demonstrating that protection was IE-exon-4 protein specific.

Numerous modifications and variations of the present invention are included in the above-identified specification and are expected to be obvious to one of skill in the art. For example, use of other appropriate non-defective adenovirus strains for construction of analogous expression systems to express the HCMV gB or IE-exon-4 gene may be constructed according to the disclosure of the present invention.

Additionally, the other subunits of HCMV major glycoprotein complexes, e.g., gcII or gcIII, or immediate-early antigens, may be expressed in a non-defective adenovirus recombinant in the same manner as described above for subunit gB. Such modifications and alterations to the compositions and processes of the present invention are believed to be encompassed in the scope of the claims appended hereto.

What is claimed is:

1. A cytomegalovirus vaccine comprising:
   a non-defective recombinant type 5 adenovirus genetically engineered to contain a Towne strain human cytomegalovirus envelope gB subunit gene, said gene being under the control of a sequence which controls expression of the gB gene product in vivo, in a suitable pharmaceutical carrier.

2. The vaccine according to claim 1 wherein said gene encodes an additional cytomegalovirus subunit protein or more than one copy of a cytomegalovirus subunit protein.

3. The vaccine according to claim 1 comprising the Ad-gB recombinant.

4. A method for inducing in a patient a protective cytotoxic T cell response to human cytomegalovirus comprising administering an effective amount of a cytomegalovirus vaccine comprising a non-defective recombinant type 5 adenovirus genetically engineered to contain a Towne strain human cytomegalovirus envelope gB subunit gene, said gene being under the control of an expression control sequence, said gB subunit being expressed in vivo by said adenovirus.

5. The method according to claim 4 comprising orally administering said vaccine.

6. The method according to claim 4 wherein an effective amount comprises $10^5$ to $10^8$ plaque forming units.

7. A non-defective recombinant type 5 strain adenovirus genetically altered to contain a portion of the human cytomegalovirus immediate early antigen gene consisting of exon-4, said portion of the gene being under the control of an expression control sequence, said adenovirus capable of expressing exon-4 in vivo.

8. The non-defective recombinant adenovirus according to claim 7, wherein the human cytomegalovirus strain is Towne.

9. A vaccine comprising a non-defective recombinant type 5 strain adenovirus genetically altered to contain a portion of the human cytomegalovirus immediate early antigen gene consisting of exon-4, said portion of the gene being under the control of an expression control sequence, said adenovirus capable of expressing exon-4 in vivo, in a suitable pharmaceutical carrier.

10. The vaccine according to claim 9, wherein the human cytomegalovirus is Towne strain.

11. A method for inducing in a patient a protective cytotoxic T cell response to human cytomegalovirus comprising administering an effective amount of a cytomegalovirus vaccine comprising a non-defective recombinant type 5 adenovirus genetically engineered to contain a portion of the human cytomegalovirus envelope immediate-early gene consisting of exon-4, said gene portion being under the control of a sequence which permits expression of the immediate-early exon-4 in vivo by said adenovirus.

\* \* \* \* \*